(12) United States Patent
Tsuchida et al.

(10) Patent No.: US 8,314,264 B2
(45) Date of Patent: Nov. 20, 2012

(54) PHOTOPOLYMERIZABLE FUNCTIONAL RADICAL-CONTAINING ORGANOSILICON COMPOUND AND MAKING METHOD

(75) Inventors: Kazuhiro Tsuchida, Annaka (JP); Yuji Yoshikawa, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 353 days.

(21) Appl. No.: 12/656,753

(22) Filed: Feb. 16, 2010

(65) Prior Publication Data
US 2010/0210862 A1 Aug. 19, 2010

(30) Foreign Application Priority Data

Feb. 17, 2009 (JP) ................................. 2009-033804

(51) Int. Cl.
*C07F 7/10* (2006.01)
(52) U.S. Cl. ...................................................... 556/421
(58) Field of Classification Search .................. None
See application file for complete search history.

(56) References Cited

U.S. PATENT DOCUMENTS

| 5,405,888 A * | 4/1995 | Takeoka ........................ 522/34 |
| 5,866,630 A | 2/1999 | Mitra et al. |
| 5,876,208 A | 3/1999 | Mitra et al. |
| 5,888,491 A | 3/1999 | Mitra et al. |
| 6,312,668 B2 | 11/2001 | Mitra et al. |
| 6,596,403 B2 | 7/2003 | Mitra et al. |

FOREIGN PATENT DOCUMENTS

| JP | 5-4994 A | 1/1993 |
| JP | 5-25219 A | 2/1993 |
| JP | 9-506104 A | 6/1997 |
| JP | 2009-242604 A | 10/2009 |
| JP | 4420668 B2 | 2/2010 |
| WO | WO 95/15740 | * 6/1995 |

OTHER PUBLICATIONS

STN Abstract of JP 04331216; Nov. 19, 1992.*
Office Action issued Jun. 29, 2011, in Japanese Patent Application No. 2009-033804.

* cited by examiner

*Primary Examiner* — Yevegeny Valenrod
(74) *Attorney, Agent, or Firm* — Birch, Stewart, Kolasch & Birch, LLP

(57) ABSTRACT

An organosilicon compound is provided comprising an organic functional radical having a photopolymerizable double bond linked to a hydrolyzable radical-bonded silicon atom via a divalent organic radical containing a urea bond. Due to the inclusion of amide, urethane or urea bond structure and a photopolymerizable functional radical, the organosilicon compound has excellent compatibility with resins. The method is capable of preparing the organosilicon compound having a minimal chlorine content.

3 Claims, 4 Drawing Sheets

PHOTOPOLYMERIZABLE FUNCTIONAL RADICAL-CONTAINING ORGANOSILICON COMPOUND AND MAKING METHOD

CROSS-REFERENCE TO RELATED APPLICATION

This non-provisional application claims priority under 35 U.S.C. §119(a) on Patent Application No. 2009-033804 filed in Japan on Feb. 17, 2009, the entire contents of which are hereby incorporated by reference.

TECHNICAL FIELD

This invention relates to an organosilicon compound having a photopolymerizable functional radical, and more particularly, to an organosilicon compound having a photopolymerizable functional radical, a urea bond, and a hydrolyzable silyl radical in the molecule, and a method for preparing the same.

BACKGROUND ART

One typical group of organosilicon compounds is silane coupling agents. The silane coupling agents have two or more different functional radicals in their molecule, and serve as a chemical bridge to bond an organic material and an inorganic material that would otherwise be difficult to bond. In the silane coupling agent, one functional radical is a hydrolyzable silyl radical which forms a silanol radical in the presence of water. This silanol radical, in turn, reacts with a hydroxyl radical on the surface of inorganic material to form a chemical bond to the inorganic material surface. The other functional radical is a reactive organic radical such as vinyl, epoxy, amino, (meth)acrylic or mercapto and forms a chemical bond with organic materials such as various synthetic resins. Due to these attributes, the silane coupling agents are widely used as modifiers, adhesive aids, and various other additives in organic and inorganic resins.

Especially, (meth)acrylic radical-containing silane coupling agents are used as modifiers for (meth)acrylic resins, adhesive aids in (meth)acrylic polymer based adhesives, and the like. The (meth)acrylic radical-containing silane coupling agents generally refer to those in which a (meth)acrylic radical is linked to a hydrolyzable silyl radical via an alkyl chain. Only a few silanes have a linking chain containing an amide or urethane bond whereas no silanes having a linking chain containing a urea bond are known.

(Meth)acrylsilane coupling agents having an amide bond are effective as adhesive aids because of intermolecular hydrogen bond by the amide bond and also compatible with resins because of their polarity. However, a problem arises with these silanes since they are generally prepared by dehydrochlorination reaction of silane coupling agents having an amino radical with (meth)acrylic acid chloride. It is difficult to remove chlorine from the resulting silanes. Such silanes can often cause degradation over time in various, applications.

There is a desire to have (meth)acrylsilanes which are highly soluble in various solvents, highly compatible with resins, substantially chlorine free, and effective as additives and modifiers.

Citation List
Patent Document 1: JP-A H05-4994
Patent Document 2: JP-A H05-25219

SUMMARY OF INVENTION

An object of the present invention is to provide an organosilicon compound containing an amide, urethane or urea bond structure and a photopolymerizable functional radical and having good compatibility with resins, and a method for preparing the organosilicon compound having a minimal chlorine content.

The inventors have found that an organosilicon compound can be prepared by reaction of an organosilicon compound containing a primary and/or secondary amino radical and a hydrolyzable radical with a specific monomer containing an amino-reactive functional radical and a photopolymerizable double bond and that the resultant compound has good compatibility with resins and a minimal chlorine content.

In one aspect, the invention provides an organosilicon compound in which an organic functional radical having a photopolymerizable double bond is linked via a divalent organic radical containing a urea bond to a silicon atom having a hydrolyzable radical bonded thereto.

In a preferred embodiment, the organosilicon compound has at least one structure of the following formula (1) in the molecule.

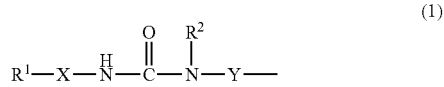

(1)

Herein $R^1$ is a (meth)acrylic radical, $R^2$ is hydrogen or a substituted or unsubstituted monovalent hydrocarbon radical which may be separated by carbonyl carbon or a heteroatom selected from the group consisting of oxygen, sulfur and nitrogen, and X and Y each are a substituted or unsubstituted divalent hydrocarbon radical which may be separated by carbonyl carbon or a heteroatom selected from the group consisting of oxygen, sulfur and nitrogen.

In a preferred embodiment, the organosilicon compound has the following general formula (2).

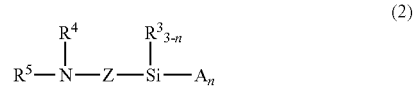

(2)

Herein A is a hydrolyzable radical, $R^3$ is each independently a substituted or unsubstituted $C_1$-$C_4$ alkyl radical, n is an integer of 1 to 3, Z is a substituted or unsubstituted $C_1$-$C_6$ alkylene radical, $R^4$ is hydrogen or a substituted or unsubstituted $C_1$-$C_8$ alkyl radical, and $R^5$ is a radical having the structure of the following formula (3) or (4):

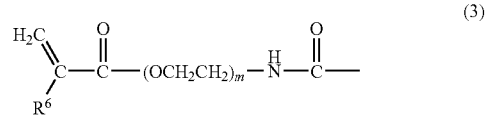

(3)

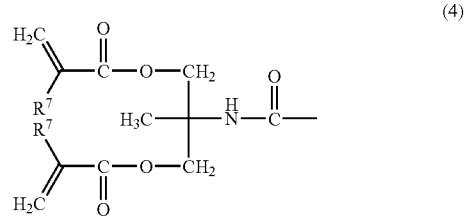

(4)

wherein $R^6$ and $R^7$ are each independently hydrogen or methyl and m is an integer of 1 to 4.

In another preferred embodiment, the organosilicon compound has the following general formula (5).

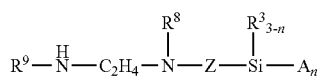
(5)

Herein A, $R^3$, n, and Z are as defined above, either one of $R^8$ and $R^9$ is a radical having the structure of the formula (3) or (4), and the other is a radical having the structure of the formula (3) or (4), hydrogen or a substituted or unsubstituted $C_1$-$C_8$ alkyl radical.

In a further preferred embodiment, the organosilicon compound has the following general formula (6).

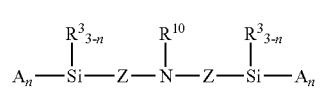
(6)

Herein A, $R^3$, n, and Z are as defined above, and $R^{10}$ is a radical having the structure of the formula (3) or (4).

In formulae (2), (5) and (6), A is preferably a $C_1$-$C_4$ alkoxy radical.

In another aspect, the organosilicon compound defined above is prepared by reacting an organosilicon compound containing a primary and/or secondary amino radical and a hydrolyzable radical with an isocyanate monomer having a photopolymerizable double bond. Preferably, the isocyanate monomer having a photopolymerizable double bond is selected from the group consisting of (meth)acryloxyethyl isocyanate, ethylene glycol-isocyanatoethyl ether mono (meth)acrylate, and 1,1-bis((meth)acryloxymethyl)ethyl isocyanate.

ADVANTAGEOUS EFFECTS OF INVENTION

The organosilicon compound of the invention exhibits high compatibility with resins due to such polar structures as hydrolyzable silyl radical, photopolymerizable functional radical, and urea bond, and is advantageously used as adhesive aids, various other additives, treating agents, modifiers for organic and inorganic materials, and the like due to hydrogen bonds formed by the urea bond structure. Upon preparation of the compound, no chlorine is involved in the reactants and reaction steps. Owing to no or minimal chlorine content, the compound has high stability and causes least degradation over time when used as an additive.

DESCRIPTION OF EMBODIMENTS

Figure 1:
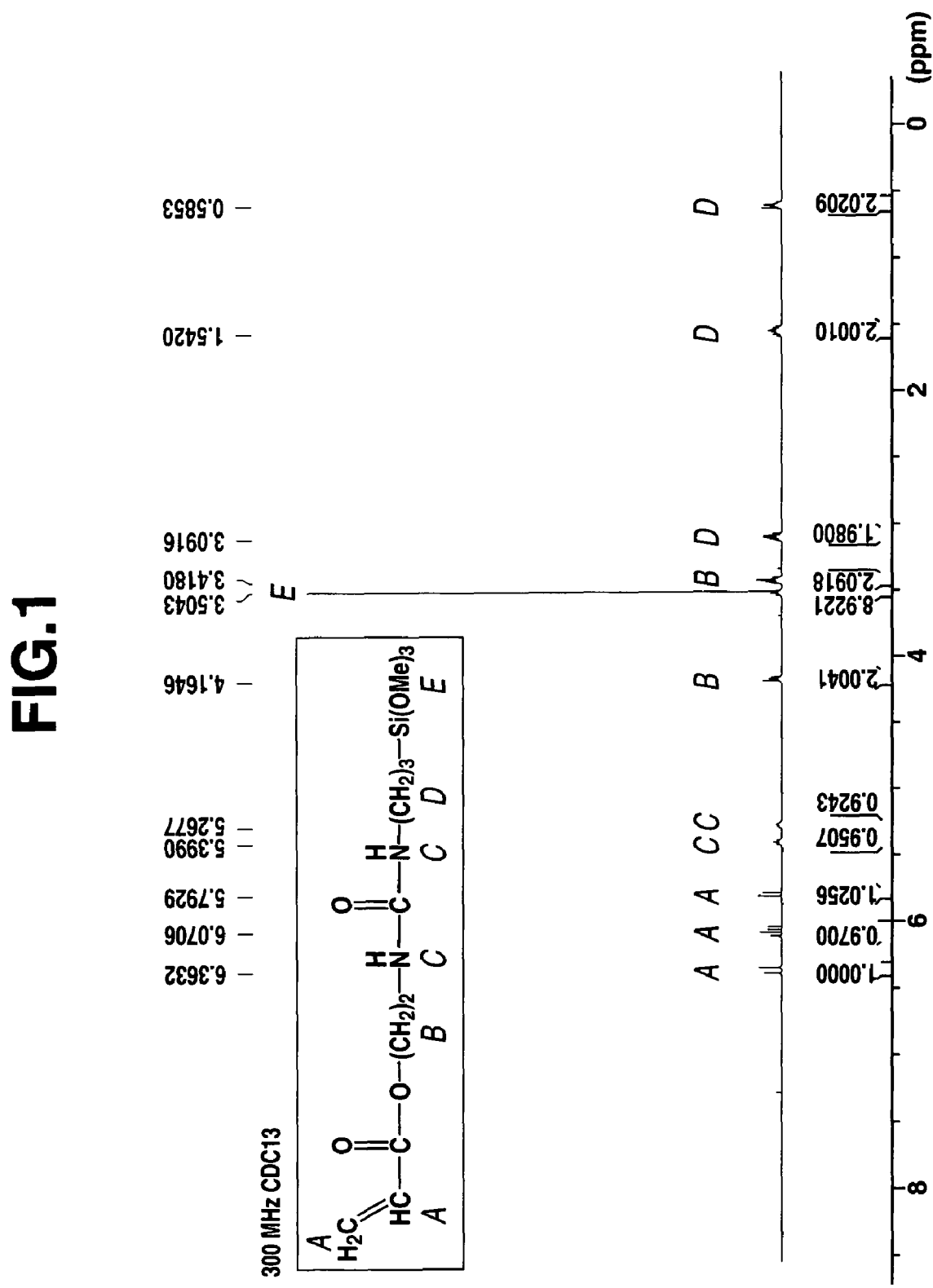
FIGS. 1 to 4 show $^1$H-NMR, $^{13}$C-NMR, $^{29}$Si-NMR, and IR spectra of the reaction product in Example 1, respectively.

The singular forms "a," "an" and "the" include plural referents unless the context clearly dictates otherwise. As used herein, the terminology "(meth)acrylic" is intended to mean acrylic or methacrylic. The notation (Cn-Cm) means a group containing from n to m carbon atoms per group.

Organosilicon Compound

The organosilicon compound of the invention comprises an organic functional radical having a photopolymerizable double bond linked to a hydrolyzable radical-bonded silicon atom through a divalent organic radical containing a urea bond. As long as this requirement is met, the compound is not particularly limited. Preferably the compound is a monomer. Examples of the organic functional radical having a photopolymerizable double bond include vinyl, acrylic, and methacrylic radicals, with acrylic and methacrylic radicals being preferred. Examples of the hydrolyzable radical bonded to a silicon atom include alkoxy radicals such as methoxy, ethoxy, propoxy and butoxy, halogen atoms such as chlorine and bromine, and acetoxy radicals. Of these, alkoxy radicals are preferred, specifically of 1 to 4 carbon atoms, with methoxy and ethoxy being most preferred.

The organic functional radical having a photopolymerizable double bond links to the divalent organic radical containing a urea bond to form a structure which preferably has the following formula (1).

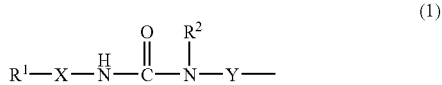
(1)

Herein $^1$ is a (meth)acrylic radical, $R^2$ is hydrogen or a substituted or unsubstituted monovalent hydrocarbon radical which may be separated by carbonyl carbon or a heteroatom selected from oxygen, sulfur and nitrogen, and X and Y each are a substituted or unsubstituted divalent hydrocarbon radical which may be separated by carbonyl carbon or a heteroatom selected from oxygen, sulfur and nitrogen.

Substituents on $R^2$, X and Y in the above structure include one or more radicals selected from the group consisting of halogen, alkyl, perfluoroalkyl, polyether, perfluoropolyether, hydrolyzable silyl, (meth)acrylic, epoxy, amino, and mercapto radicals. Of these, alkyl, hydrolyzable silyl and (meth) acrylic radicals are preferred. The monovalent hydrocarbon radicals of le are preferably those of 1 to 20 carbon atoms and more preferably of 1 to 10 carbon atoms, and include alkyl, alkenyl, aryl, and cycloalkyl radicals. The divalent hydrocarbon radicals of X and Y are preferably those of 1 to 20 carbon atoms and more preferably of 1 to 10 carbon atoms, and include alkylene and arylene radicals.

The preferred organosilicon compounds have the following general formulae (2), (5) and (6).

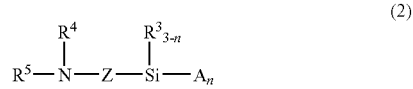
(2)

In formula (2), A is a hydrolyzable radical, $R^3$ is each independently a substituted or unsubstituted $C_1$-$C_4$ alkyl radical, n is an integer of 1 to 3, Z is a substituted or unsubstituted $C_1$-$C_6$ alkylene radical, $R^4$ is hydrogen or a substituted or unsubstituted $C_1$-$C_8$ alkyl radical, and $R^5$ is a radical having the structure of the following formula (3) or (4):

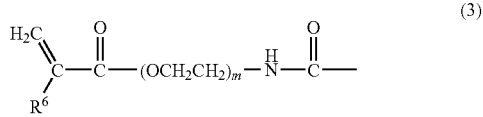
(3)

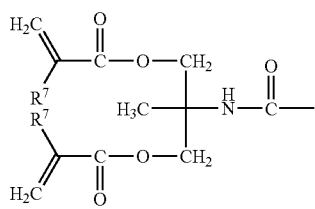

(4)

wherein $R^6$ and $R^7$ are each independently hydrogen or methyl and m is an integer of 1 to 4.

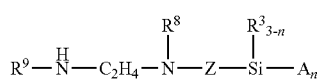

(5)

In formula (5), A is a hydrolyzable radical, $R^3$ is each independently a substituted or unsubstituted $C_1$-$C_4$ alkyl radical, n is an integer of 1 to 3, Z is a substituted or unsubstituted $C_1$-$C_6$ alkylene radical, either one of $R^8$ and $R^9$ is a radical having the structure of the following formula (3) or (4):

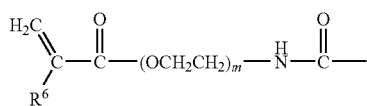

(3)

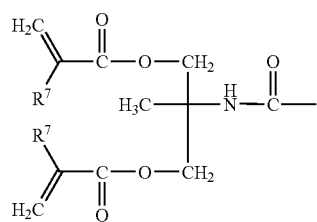

(4)

wherein $R^6$ and $R^7$ are each independently hydrogen or methyl and m is an integer of 1 to 4, and the other is a radical having the structure of the formula (3) or (4), hydrogen or a substituted or unsubstituted $C_1$-$C_8$ alkyl radical.

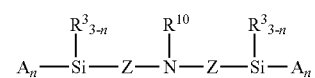

(6)

In formula (6), A is independently a hydrolyzable radical, $R^3$ is each independently a substituted or unsubstituted $C_1$-$C_4$ alkyl radical, n is an integer of 1 to 3, Z is a substituted or unsubstituted $C_1$-$C_6$ alkylene radical, and $R^{10}$ is a radical having the structure of the following formula (3) or (4):

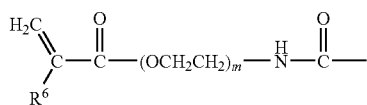

(3)

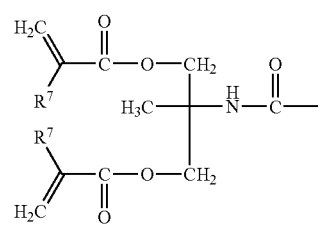

(4)

wherein $R^6$ and $R^7$ are each independently hydrogen or methyl and m is an integer of 1 to 4.

In formulae (2), (5) and (6), A is a hydrolyzable radical, examples of which include alkoxy radicals such as methoxy, ethoxy, propoxy and butoxy, halogen atoms such as chlorine and bromine, and acetoxy radicals. Of these, alkoxy radicals are preferred, with $C_1$-$C_4$ alkoxy radicals being more preferred. Most preferred are methoxy and ethoxy. $R^3$ is each independently a substituted or unsubstituted $C_1$-$C_4$ alkyl radical, examples of which include methyl, ethyl, n-propyl, isopropyl, n-butyl, and isobutyl. The subscript n is an integer of 1 to 3 and preferably 2 or 3.

$R^4$ in formula (2) is independently hydrogen or a substituted or unsubstituted $C_1$-$C_8$ alkyl radical. Examples include hydrogen, methyl, ethyl, propyl, isopropyl, butyl, isobutyl, tert-butyl, pentyl, hexyl, cyclohexyl, and octyl. Examples of Z in formulae (2), (5) and (6) include, but are not limited to, methylene, ethylene, propylene, 1-methylpropylene, 2-methylpropylene, 3-methylpropylene, and butylene.

Examples of the organosilicon compound containing a photopolymerizable double bond and a urea bond in the molecule are given by the following structural formulae (7) to (15) wherein Me is methyl.

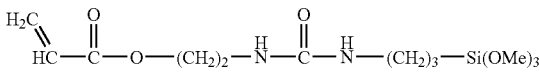

(7)

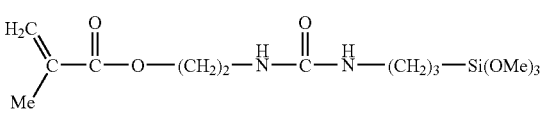

(8)

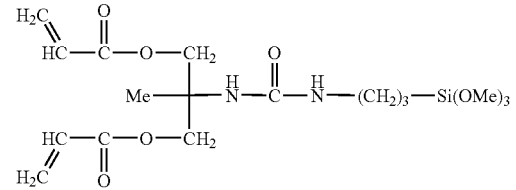

(9)

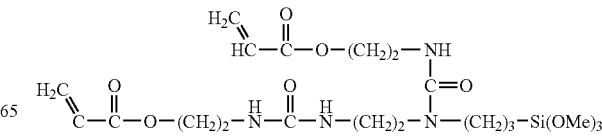

(10)

-continued

(11)
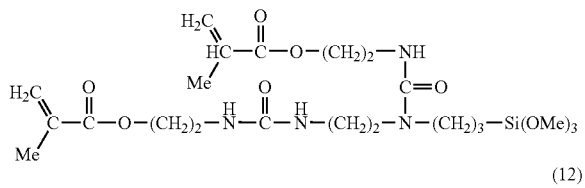

(12)
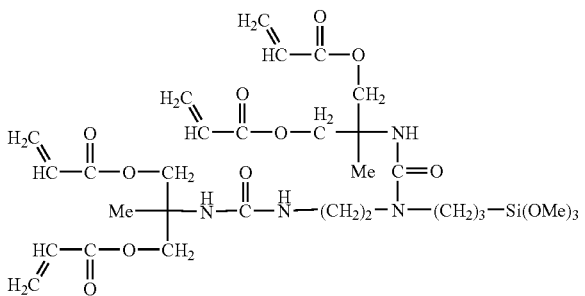

(13)
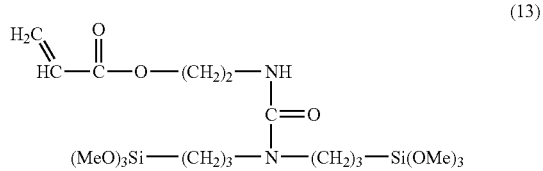

(14)
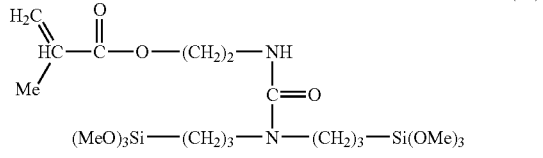

(15)
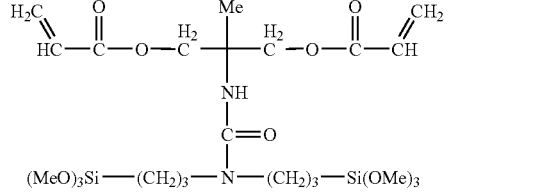

Also included are those compounds of the above formulae in which methoxy is replaced by ethoxy.

Method

The organosilicon compound of the invention may be prepared by reaction of an organosilicon compound containing a primary and/or secondary amino radical and a hydrolyzable radical with an isocyanate compound having a photopolymerizable radical. To distinguish the organosilicon compound of the invention and the starting organosilicon compound containing a primary and/or secondary amino radical and a hydrolyzable radical, the former is referred to as the target organosilicon compound and the latter is referred to as the organosilicon reactant, hereinafter.

A solvent may be used in the production of the target organosilicon compound, if desired. The solvent used is not particularly limited as long as it is nonreactive with the reactants, aminosilane and isocyanate compounds. Examples include aliphatic hydrocarbon solvents such as pentane, hexane, heptane and decane, ether solvents such as diethyl ether, tetrahydrofuran and 1,4-dioxane, amide solvents such as formamide, dimethylformamide and N-methylpyrrolidone, and aromatic hydrocarbon solvents such as benzene, toluene and xylene.

The reaction to produce the target organosilicon compound is exothermic. Since side reactions can occur at unnecessarily high temperatures, the reaction temperature is preferably controlled in a range of −10° C. to 150° C., more preferably 0° C. to 100° C., and most preferably 5° C. to 50° C. Below −10° C., the reaction rate may be retarded, resulting in a decline of productivity. Also maintaining such low temperature is unpractical because a special production system is needed. A temperature of higher than 150° C. may cause side reactions such as polymerization of polymerizable functional radicals.

The reaction time required to produce the target organosilicon compound is not particularly limited as long as the above-mentioned temperature management during exothermic reaction is possible and the exothermic reaction is brought to completion. The reaction time is preferably about 10 minutes to about 24 hours and more preferably about 1 hour to about 10 hours.

The organosilicon reactant used in the production of the target organosilicon compound is not particularly limited as long as it has a primary and/or secondary amino radical and a hydrolyzable radical. Suitable organosilicon reactants include α-aminomethyltrimethoxysilane,
α-aminomethylmethyldimethoxysilane,
α-aminomethyldimethylmethoxysilane,
α-aminomethyltriethoxysilane,
α-aminomethylmethyldiethoxysilane,
α-aminomethyldimethylethoxysilane,
γ-aminopropyltrimethoxysilane,
γ-aminopropylmethyldimethoxysilane,
γ-aminopropyldimethylmethoxysilane,
γ-aminopropyltriethoxysilane,
γ-aminopropylmethyldiethoxysilane,
γ-aminopropyldimethylethoxysilane,
N-(2-aminoethyl)-α-aminomethyltrimethoxysilane,
N-(2-aminoethyl)-α-aminomethylmethyldimethoxysilane,
N-(2-aminoethyl)-α-aminomethyldimethylmethoxysilane,
N-(2-aminoethyl)-α-aminomethyltriethoxysilane,
N-(2-aminoethyl)-α-aminomethylmethyldiethoxysilane,
N-(2-aminoethyl)-α-aminomethyldimethylethoxysilane,
bis(trimethoxysilylpropyl)amine,
bis(methyldimethoxysilylpropyl)amine,
bis(dimethylmethoxysilylpropyl)amine,
bis(triethoxysilylpropyl)amine,
bis(methyldiethoxysilylpropyl)amine, and
bis(dimethylethoxysilylpropyl)amine.

The other reactant used in the production of the target organosilicon compound is an isocyanate compound which is not particularly limited as long as it has a photopolymerizable radical. Examples of the isocyanate compounds which are commercially available from chemical suppliers include (meth)acryloxyethyl isocyanate, ethylene glycol-isocyanatoethyl ether mono(meth)acrylate, and 1,1-bis((meth)acryloxymethyl)ethyl isocyanate.

In the production of the target organosilicon compound, the organosilicon reactant comprising a primary and/or secondary amino radical and a hydrolyzable radical and the isocyanate compound having a photopolymerizable radical may be combined at any desired ratio. It is preferred from the aspects of reactivity and productivity that 0.5 to 3 moles and more preferably 0.8 to 2.5 moles of the isocyanate compound be reacted with one mole of the organosilicon reactant. If the amount of the isocyanate compound added is too small, a noticeable fraction of the organosilicon reactant may remain unreacted. Although the remaining reactant does not affect the physical properties of the target silane, there result disadvantages like low purity and reduced productivity. If used in too much amounts, the isocyanate compound may polymerize by itself, eventually leading to gelation.

The reaction of an amino radical with an isocyanate radical forms a urea bond, resulting in the target organosilicon compound. The target organosilicon compound is useful as a silane coupling agent.

EXAMPLE

Examples of the invention are given below by way of illustration and not by way of limitation. In Examples, the viscosity is measured at 25° C. by a capillary viscometer. The specific gravity and refractive index are also measured at 25° C. Nuclear magnetic resonance spectroscopy and infrared spectroscopy are abbreviated as NMR and IR, respectively. Me stands for methyl.

Example 1

Figure 2:
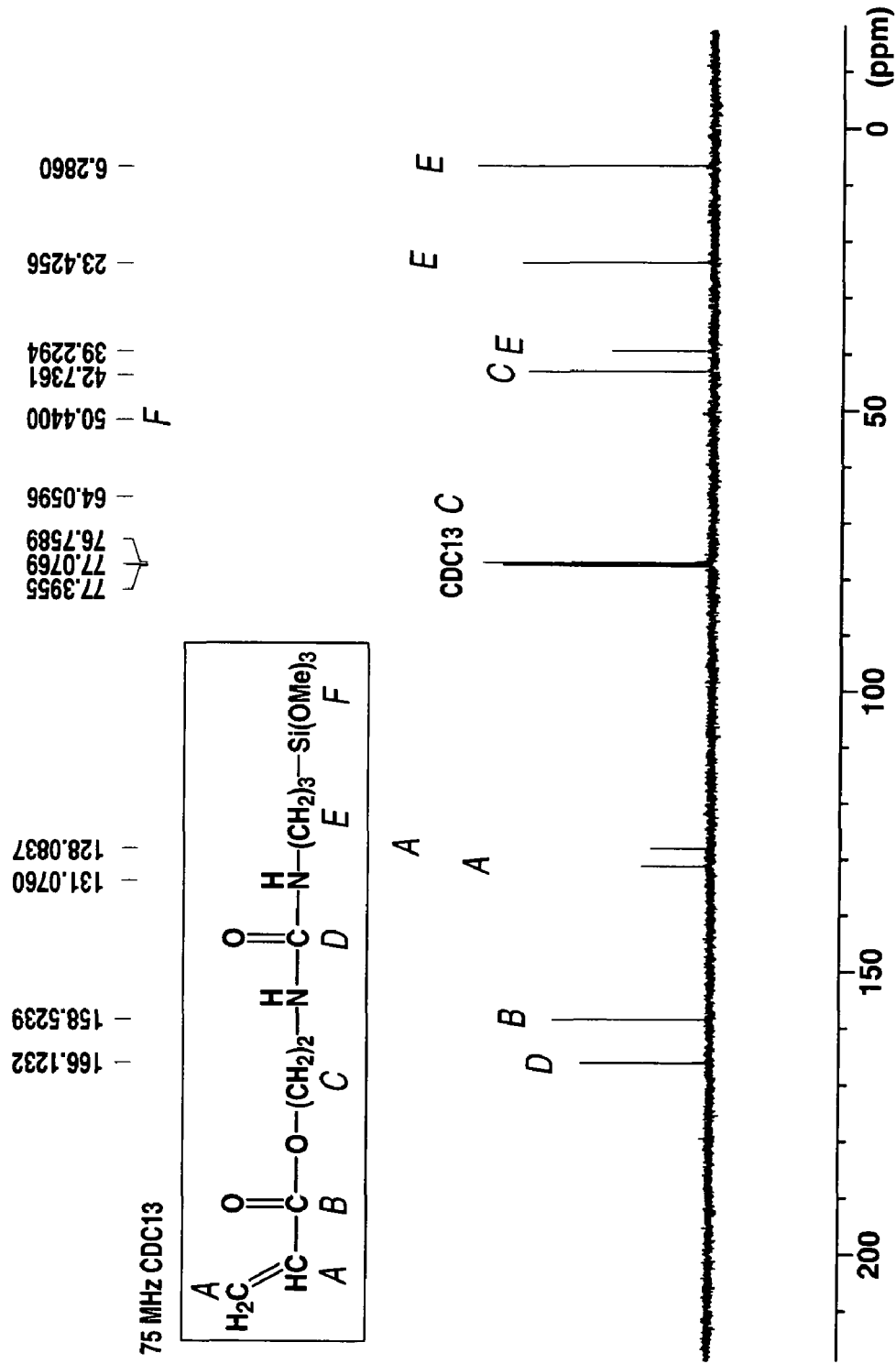
Figure 3:
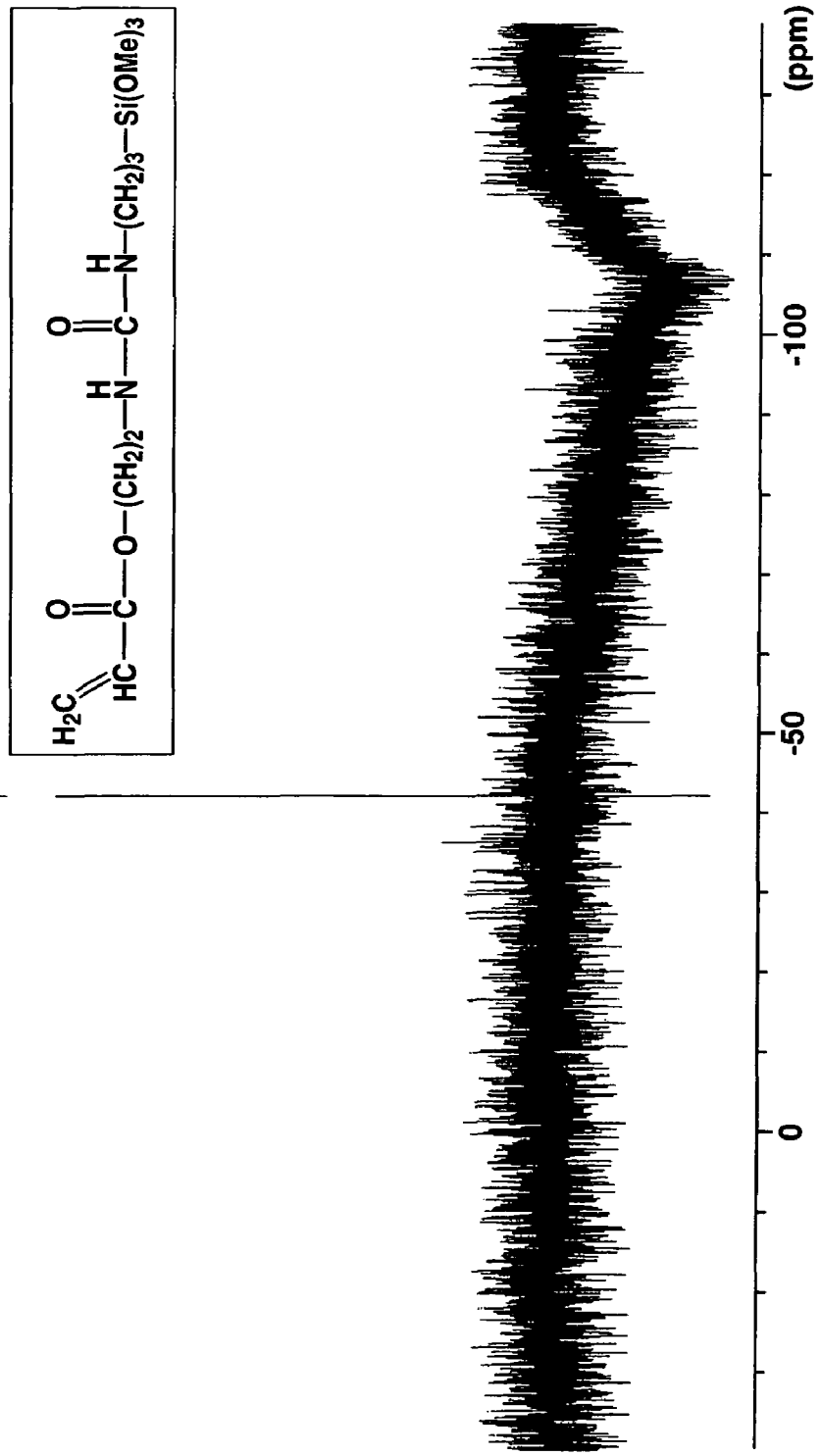
Figure 4:
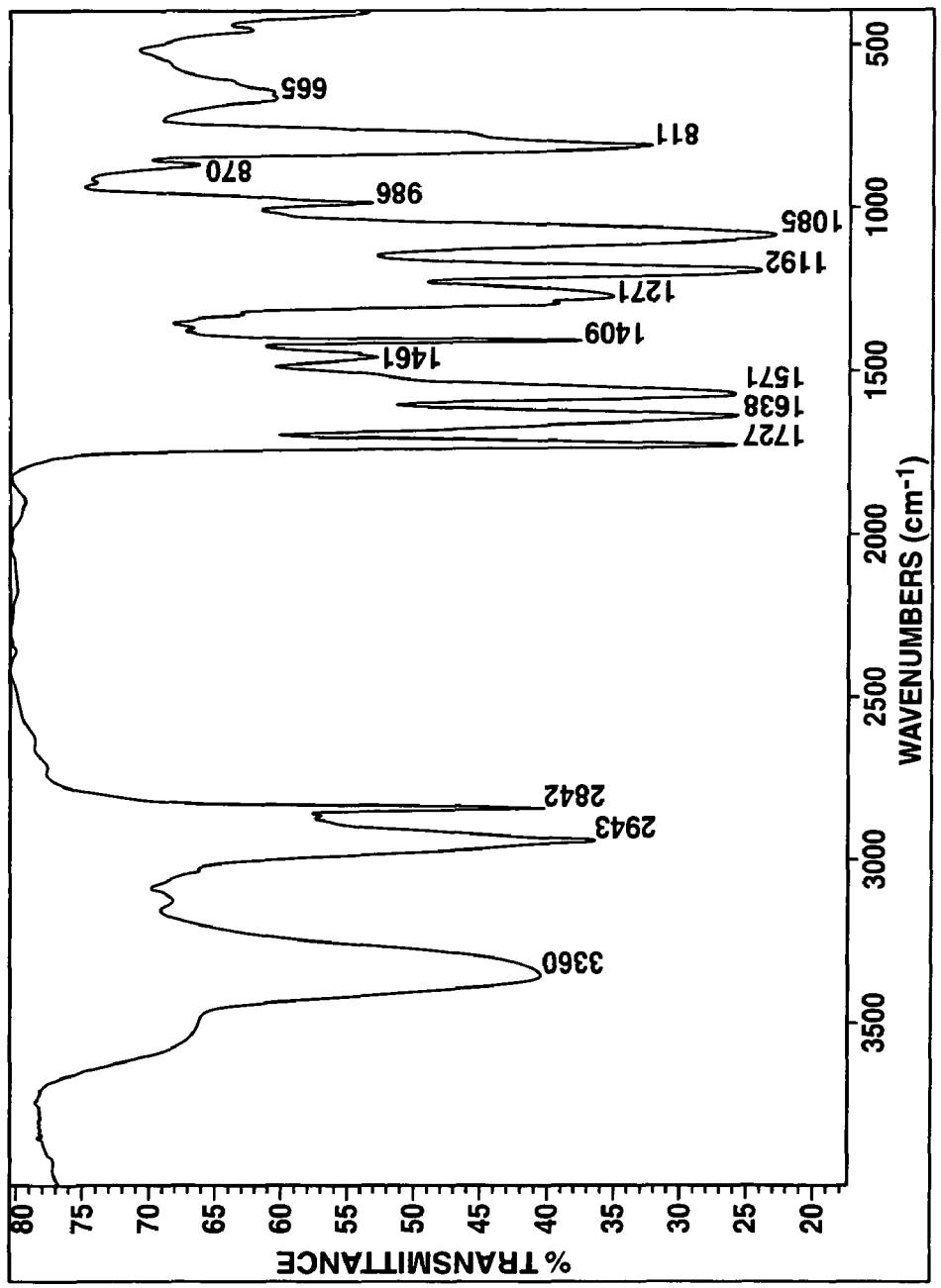

A 1-L separable flask equipped with a stirrer, reflux condenser, dropping funnel and thermometer was charged with 179.3 g (1.00 mol) of γ-aminopropyltrimethoxysilane (KBM-903, Shin-Etsu Chemical Co., Ltd.) and cooled to 0° C. in an ice bath. To the flask 141.2 g (1.00 mol) of acryloxyethyl isocyanate (Karenz AOI, Showa Denko K. K.) was added dropwise. The contents were stirred for 4 hours while heating at 30° C. The end of reaction was determined by IR analysis as the complete disappearance of absorption peaks assigned to an isocyanate radical of the reactant and the appearance of absorption peaks assigned to a urea bond instead. The resulting reaction product was a pale yellow liquid having a viscosity of 307 mm$^2$/s, a specific gravity of 1.143, and a refractive index of 1.4673. On NMR spectroscopy, the reaction product was identified to be a single compound having the following chemical structural formula (7). FIGS. 1, 2, 3 and 4 show $^1$H-NMR, $^{13}$C-NMR, $^{29}$Si-NMR, and IR spectra of the compound, respectively.

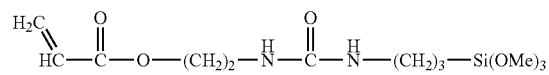

(7)

Example 2

A 1-L separable flask equipped with a stirrer, reflux condenser, dropping funnel and thermometer was charged with 179.3 g (1.00 mol) of γ-aminopropyltrimethoxysilane (KBM-903, Shin-Etsu Chemical Co., Ltd.) and cooled to 0° C. in an ice bath. To the flask 239.0 g (1.00 mol) of 1,1-bis(acryloxymethyl)-ethyl isocyanate (Karenz BEI, Showa Denko K. K.) was added dropwise. The contents were stirred for 4 hours while heating at 30° C. The end of reaction was determined by IR analysis as the complete disappearance of absorption peaks assigned to an isocyanate radical of the reactant and the appearance of absorption peaks assigned to a urea bond instead. The resulting reaction product was a pale yellow liquid having a viscosity of 3,424 mm$^2$/s, a specific gravity of 1.151, and a refractive index of 1.4747. On NMR spectroscopy, the reaction product was identified to be a single compound having the following chemical structural formula (9).

(9)

NMR spectroscopy data of the compound are shown below.

$^1$H-NMR (300 MHz, CDCl$_3$, δ (ppm)): 0.70 (t, 2H), 1.46 (s, 3H), 1.69 (quint, 2H), 3.22 (t, 2H), 3.40 (t, 2H), 3.46 (s, 9H), 4.58 (m, 4H), 5.42 (m, 2H), 5.84 (m, 1H), 5.90 (m, 1H), 6.02 (m, 2H), 6.32 (m, 2H)

$^{13}$C-NMR (75 MHz, CDCl$_3$, δ (ppm)): 6.3, 20.3, 23.9, 42.8, 50.3, 54.9, 66.7, 128.3, 130.7, 158.4, 165.5

$^{29}$Si-NMR (60 MHz, CDCl$_3$, δ (ppm)): −42.2

Example 3

A 1-L separable flask equipped with a stirrer, reflux condenser, dropping funnel and thermometer was charged with 222.4 g (1.00 mol) of N-(2-aminoethyl)-γ-aminopropyl-trimethoxysilane (KBM-603, Shin-Etsu Chemical Co., Ltd.) and cooled to 0° C. in an ice bath. To the flask 478.0 g (2.00 mol) of 1,1-bis(acryloxymethyl)ethyl isocyanate (Karenz BEI, Showa Denko K. K.) was added dropwise. The contents were stirred for 4 hours while heating at 30° C. The end of reaction was determined by IR analysis as the complete disappearance of absorption peaks assigned to an isocyanate radical of the reactant and the appearance of absorption peaks assigned to a urea bond instead. The resulting reaction product was a highly viscous colorless clear fluid having a refractive index of 1.4914. On NMR spectroscopy, the reaction product was identified to be a single compound having the following chemical structural formula (12).

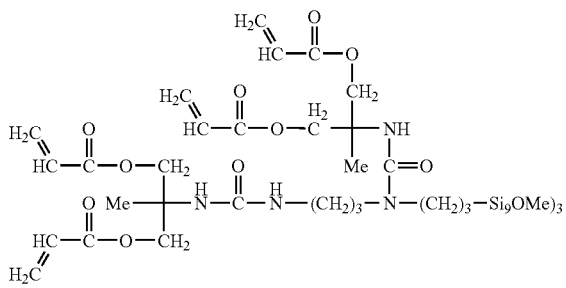

(12)

NMR spectroscopy data of the compound are shown below.

$^1$H-NMR (300 MHz, CDCl$_3$, δ (ppm)): 0.54 (t, 2H), 1.40 (s, 3H), 1.48 (s, 3H), 1.57 (quint, 2H), 3.17 (t, 2H), 3.40 (s, 9H), 4.50 (m, 4H), 4.56 (m, 4H), 5.42 (m, 4H), 5.96 (m, 4H), 6.23 (m, 1H), 6.27 (m, 4H), 6.40 (m, 1H), 6.89 (m, 1H)

$^{13}$C-NMR (75 MHz, CDCl$_3$, δ (ppm)): 6.7, 20.2, 20.4, 22.4, 39.5, 47.2, 50.2, 50.5, 54.9, 55.8, 66.6, 128.4, 128.5, 130.5, 130.7, 157.8, 159.1, 165.4, 165.7

$^{29}$Si-NMR (60 MHz, CDCl$_3$, δ (ppm)): −42.4

Example 4

A 1-L separable flask equipped with a stirrer, reflux condenser, dropping funnel and thermometer was charged with 341.6 g (1.00 mol) of bis(trimethoxysilylpropyl)amine (KBM-666P, Shin-Etsu Chemical Co., Ltd.) and cooled to 0° C. in an ice bath. To the flask 141.2 g (1.00 mol) of acryloxyethyl isocyanate (Karenz AOI, Showa Denko K. K.) was added dropwise. The contents were stirred for 4 hours while heating at 30° C. The end of reaction was determined by IR analysis as the complete disappearance of absorption peaks assigned to an isocyanate radical of the reactant and the appearance of absorption peaks assigned to a urea bond instead. The resulting reaction product was a pale yellow liquid having a viscosity of 165 mm²/s, a specific gravity of 1.130, and a refractive index of 1.4606. On NMR spectroscopy, the reaction product was identified to be a single compound having the following chemical structural formula (13).

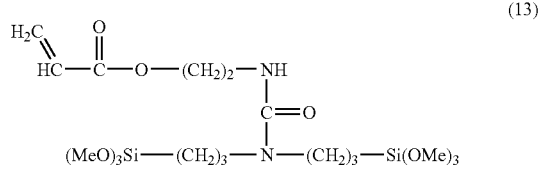

(13)

NMR spectroscopy data of the compound are shown below.

$^1$H-NMR (300 MHz, CDCl$_3$, δ (ppm)): 0.49 (t, 4H), 1.53 (quint, 4H), 3.06 (t, 4H), 3.40 (t, 2H), 3.46 (s, 18H), 4.14 (t, 2H), 5.16 (m, 1H), 5.73 (m, 1H), 6.04 (s, 1H), 6.30 (m, 1H)

$^{13}$C-NMR (75 MHz, CDCl$_3$, δ (ppm)): 5.8, 21.5, 40.0, 49.2, 50.4, 64.0, 128.2, 130.8, 157.4, 166.1

$^{29}$Si-NMR (60 MHz, CDCl$_3$, δ (ppm)): -42.0

Japanese Patent Application No. 2009-033804 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound having the following general formula (6):

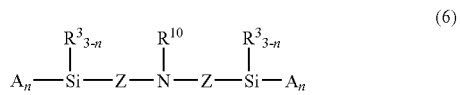

(6)

wherein
A is independently a hydrolyzable radical,
each R$^3$ is independently a substituted or unsubstituted C$_1$-C$_4$ alkyl radical,
n is an integer of 1 to 3,
Z is a substituted or unsubstituted C$_1$-C$_6$ alkylene radical, and
R$^{10}$ is a radical having the structure of the following formula (4):

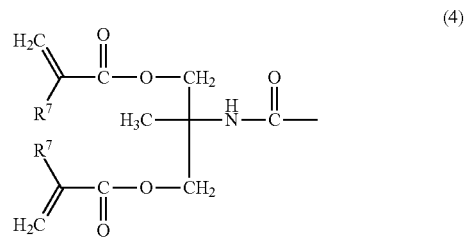

(4)

wherein each R$^7$ is independently hydrogen or methyl.

2. The compound of claim 1, wherein A is a C$_1$-C$_4$ alkoxy radical.

3. A method for preparing the organosilicon compound of claim 1, comprising reacting an organosilicon compound selected from the group consisting of
bis(trimethoxysilylpropyl)amine,
bis(methyldimethoxysilylpropyl)amine,
bis(dimethylmethoxysilylpropyl)amine,
bis(triethoxysilylpropyl)amine,
bis(methyldiethoxysilylpropyl)amine, and
bis(dimethylethoxysilylpropyl)amine
with an isocyanate monomer having a photopolymerizable double bond.

* * * * *